July 15, 1969 A. W. KENNON Plant Pat. 2,906
APRICOT TREE
Filed Dec. 18, 1967
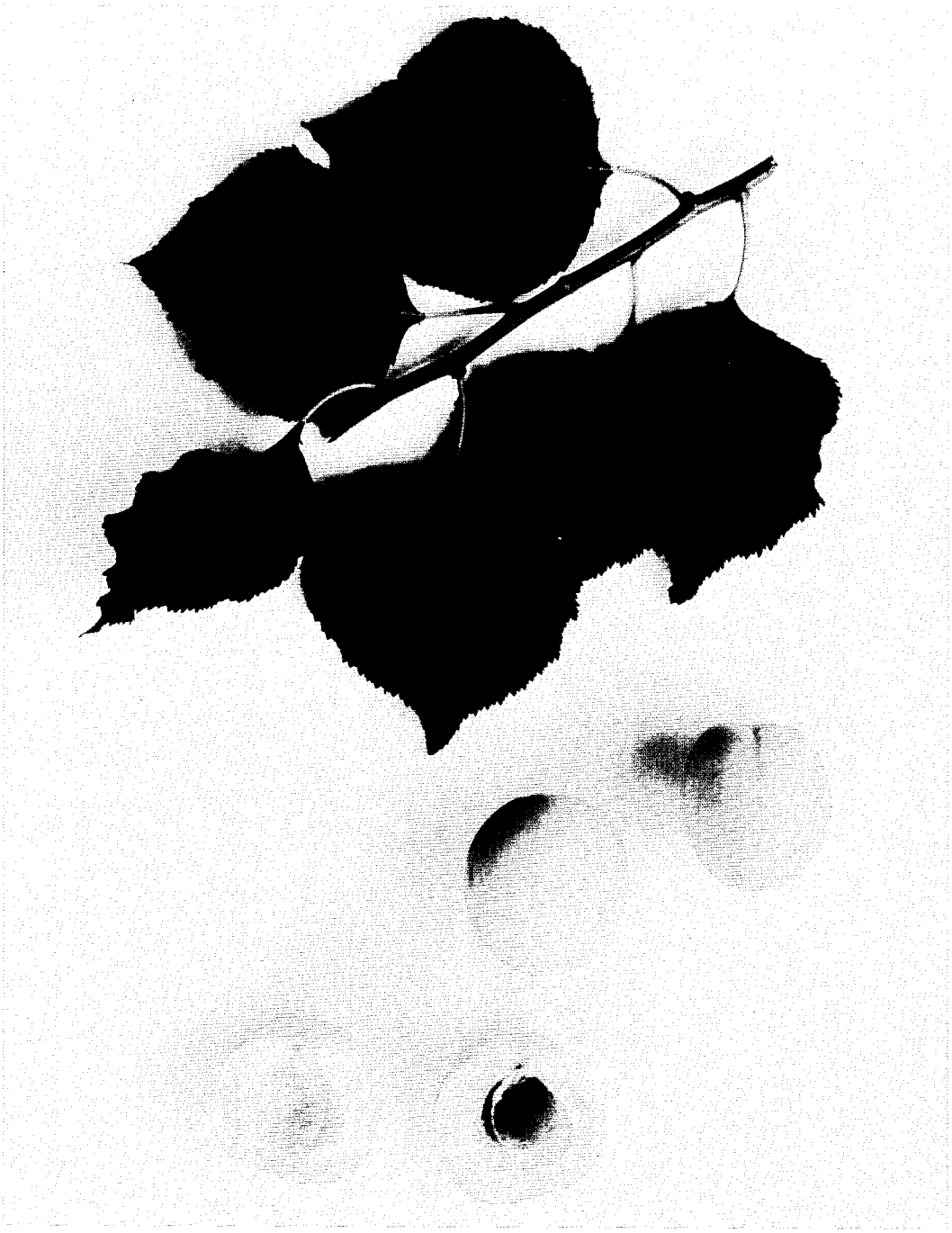
INVENTOR
Andrew W. Kennon
BY Webster & Webster
ATTORNEYS

United States Patent Office

Plant Pat. 2,906
Patented July 15, 1969

2,906
APRICOT TREE

Andrew W. Kennon, 2870 Fallon Road,
Hollister, Calif. 95203

Filed Dec. 18, 1967, Ser. No. 691,665
Int. Cl. A01h *5/08*
U.S. Cl. Plt.—39 1 Claim

ABSTRACT OF THE DISCLOSURE

A variety of apricot tree which is large, vigorous, spreading, vase-formed, and dense in growth; the tree being a regular and very productive bearer of medium size, late ripening freestone fruit having yellow flesh, and yellow skin.

Origin of the variety

The present variety of apricot tree originated as a mutation limb—discovered by me—growing on a Royal Blenheim (unpatented) tree in an orchard on a ranch, of which I am an owner, located near Hollister, in San Benito County, Calif. Upon recognition by me of the novel characteristics of the variety, as hereinafter described, it was asexually reproduced in the following manner.

Asexual reproduction of the variety

This was successfully accomplished, on my behalf, by grafting scions from the original mutation limb on apricot seedlings grown on the aforementioned ranch; such grafts having run true to said mutation limb in all respects.

Summary of the variety

The present variety of apricot tree is large, vigorous, spreading, vase-formed, dense, self-fertile, and particularly characterized by the regular and very productive bearing of medium size, late ripening, freestone fruit; such fruit having yellow flesh, and yellow skin, the skin at the suture line being a more pronounced yellow than elsewhere.

In comparison to the Royal Blenheim, the fruit of the herein claimed variety of apricot tree ripens and is in harvest about seven to eight weeks later.

Brief description of the drawing

The drawing is an illustration, by photographic reproduction in color, of a twig with leaves, and detached fruit; one fruit being cut in half to expose the flesh, and with the stone remaining in one cut half.

Description of the variety

The botanical details of this new and distinct variety of apricot tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Density.*—Dense.
- *Form.*—Vase-formed.
- *Hardiness.*—Hardy.
- *Production.*—Very productive.
- *Bearing.*—Regular bearer.
- *Fertility.*—Self-fertile.

Trunk:
- *Size.*—Medium.
- *Texture.*—Medium.

Branches:
- *Size.*—Medium.

- *Texture.*—Medium.
- *Color.*—First year's growth—green. Mature growth—red to brown.

Leaves:
- *Size.*—Medium. Average length—3⅛″. Average width—2⅝″.
- *Form.*—Ovate; acutely pointed.
- *Thickness.*—Medium.
- *Texture.*—Smooth.
- *Margin.*—Crenate.
- *Petiole.*—Medium length.
- *Glands.*—Number and position—average 1 to 3 on petiole.
- *Stipules.*—None.
- *Color.*—Top side—Medium Green (23–L–9). Under side—Lighter Green (22–K–7).

Flower buds: Size, form, and color substantially the same as Royal Blenheim apricot.

Flowers:
- *Blooming period.*—Date of first bloom—Feb. 28, 1967. Date of full bloom—Mar. 8, 1967. Size, form, and color substantially the same as Royal Blenheim apricot. To prove self-fertility of the variety, tree was masked prior to blooming.

Fruit:
- *Maturity when described.*—Hard ripe—Sept. 15, 1967.
- *Date of first picking.*—Sept. 15, 1967.
- *Date of last picking.*—Oct. 1, 1967.
- *Size.*—Uniform; medium. Average diameter axially—2″. Average transversely in suture plane—1⅞″.
- *Form.*—Uniform; symmetrical; globose to oblong; compressed laterally.
- *Suture.*—A distinct line extending from base to apex with slight depression beyond pistil point.
- *Ventral surface.*—Rounded slightly.
- *Cavity.*—Elongated in suture plane with suture showing on one side. Average depth—3/16″. Average breadth—½″.
- *Base.*—Rounded to truncate.
- *Apex.*—Short to depressed.
- *Pistil point.*—Inconspicuous.

Skin:
- *Thickness.*—Medium.
- *Texture.*—Medium.
- *Tendency to crack.*—Slight.
- *Down.*—Scant.
- *Color.*—Yellow (11–L–4) with very slight orange blush. Yellow more pronounced at the suture line.

Flesh:
- *Texture.*—Medium.
- *Fibers.*—Few; tender.
- *Ripens.*—Evenly.
- *Flavor.*—Subacid; delicate; vinous.
- *Aroma.*—Distinct.
- *Eating quality*—Good to best.
- *Color.*—Yellow (11–L–5).

Stone:
- *Type.*—Free.
- *Size.*—Small. Average length—⅞″. Average breadth—¾″. Average thickness—½″.
- *Form.*—Globose to oblong.
- *Base.*—Oblique.
- *Sides.*—Equal.
- *Color.*—Brown (8–J–11).

Use: Market—local; dessert.
Keeping quality: Good to medium.
Shipping quality: Medium.

The apricot tree and its fruit herein described may vary in slight detail due to climatic and soil conditions under which the variety may be grown; the present description being of the variety as grown in the agricultural area near Hollister, San Benito County, Calif., and wherein in 1967 all fruit ripened over two weeks later than normal.

I claim:

1. A new and distinct variety of apricot tree, substantially as illustrated and described, which is large, vigorous, spreading, vase-formed, dense, self-fertile and particularly characterized by the regular and very productive bearing of medium size freestone fruit which ripens approximately seven to eight weeks later than the Royal Blenheim, and which fruit has yellow flesh and yellow skin, the skin at the suture line being a more pronounced yellow than elsewhere.

No references cited.

ROBERT E. BAGWELL, Primary Examiner